United States Patent [19]

Kuzmanovich

[11] Patent Number: 4,838,854

[45] Date of Patent: Jun. 13, 1989

[54] METHOD AND APPARATUS FOR SELECTING A MEDICINE INJECTION SITE

[76] Inventor: Zivko Kuzmanovich, 16030 Cantlay St., Van Nuys, Calif. 91406

[21] Appl. No.: 189,823

[22] Filed: May 3, 1988

[51] Int. Cl.⁴ .............................................. A61M 5/00
[52] U.S. Cl. ...................................... 604/49; 604/116
[58] Field of Search .................. 604/116, 49; 401/427, 401/429

[56] References Cited

U.S. PATENT DOCUMENTS

| | | | |
|---|---|---|---|
| 2,011,545 | 8/1935 | Thorp | 401/129 |
| 4,219,283 | 8/1980 | Buckley et al. | 401/129 |
| 4,527,575 | 7/1985 | Vasas | 401/129 |

Primary Examiner—Stephen C. Pellegrino
Attorney, Agent, or Firm—Jack C. Munro

[57] ABSTRACT

An apparatus and a method to aid a human being in correctly selecting the site of a medicine injection when that human being is required to take a series of medicine injections on a regular basis. The apparatus comprises a small container which includes a small brush which is attached to a cap. Within the container is to be located an opaque liquid. The cap is to be removed from the container and positioned directly against the site of the current injection and with the brush then contacting the skin leaving an opaque mark to denote the site of the next succeeding injection.

1 Claim, 1 Drawing Sheet

METHOD AND APPARATUS FOR SELECTING A MEDICINE INJECTION SITE

BACKGROUND OF THE INVENTION

The field of this invention relates to injections of medicine by a syringe and more particularly to an apparatus to aid individual who self-administers injections on a regular basis to avoid overlapping injection points which could cause tissue damage and/or infection.

The subject matter of this invention is discussed primarily in conjunction with diabetics whom are required to self-administer an insulin injection on a daily basis. However, it is to be understood that the subject matter of this invention could be applicable to any individual who is required to self-administer medicine or administer to others through the use of a syringe on a regular basis.

Diabetics are instructed that there are six areas on the human body that are available for site injection of insulin. These six sites are the upper portion of the right and left arms, the right and left thighs, and the right and left sides of the abdomen. Each area can accommodate a plurality of injections. For example, each area can accommodate at least eight injection points. The recommended procedure is to pick one area and progressively go through those eight injection points and then move to a second area and repeat the process, and so forth. Finally, when the individual has proceeded through all six areas, that individual is then to go back to the first area and repeat the procedure with adequate time having been past to insure that complete healing has occurred of the first area prior to the now administering of the next series of injections.

It is recommended that within each injection area the minimum distance from one injection point to the next injection point be at least one and one-half inches. It is common that the diabetic guess at the site of the last injection and then measure what is believed to be approximately one and one-half inches and then make the current injection. It is common that the diabetic becomes confused and administers an injection too near the previous injection, or applies an injection at an area that was only injected a few days ago.

In the past, in order to aid the diabetic in administering of the injection at the proper locations, there has been provided a chart. This chart is to be placed against the skin at the desired area with this chart being divided into a series of separate locations. The diabetic is to proceed through these locations in a particular sequence until each location is to be utilized. However, the diabetic may not always apply the chart to the area at exactly the same point. Also, the diabetic may lose track at exactly what point in the sequence the current injection is to occur.

SUMMARY OF THE INVENTION

The structure of the present invention is directed to a small container within which is located a small quantity of an opaque liquid. The composition of this opaque liquid is to resist dissolving by water, but yet would be easily dissolvable with a disinfecting liquid such as alcohol. A cap is removably secured to the container with this cap including a handle section to facilitate removing of the cap from the container. Attached to the cap is a thin rod which terminates in a pointed brush. The distance from the tip of the brush to the forwardmost edge of the cap is to be one and one-half inches. With the cap removed from the container, this forward edge of the cap is to be placed at a desired location against the skin with the tip of the brush then contacting the skin denoting a location exactly one and one-half inches from the edge of the cap. The cap is then to be remounted onto the container with medicine injection to occur at the site of contact of the forward edge of the cap on the skin.

An advantage of the present invention is that the structure and method will make obsolete all previous complicated ways of selecting injection site locations.

Another objective of the present invention is to alleviate the user from the maintaining of any kind of a written record to denote the sequence of injection sites.

Another objective of the present invention is to alleviate the administrating individual the responsibility of determining injection locations which can be especially cumbersome for non-educated individuals, or for individuals with poor or impaired memories.

The primary objective of the present invention is to insure that tissue damage is avoided in diabetic individuals, or to any individual that is on a daily injection program.

Another objective of the present invention is that it can be manufactured at an inexpensive cost and, therefore can be sold to the ultimate consumer at an inexpensive price.

DETAILED DESCRIPTION OF THE SHOWN EMBODIMENT

Figure 1:
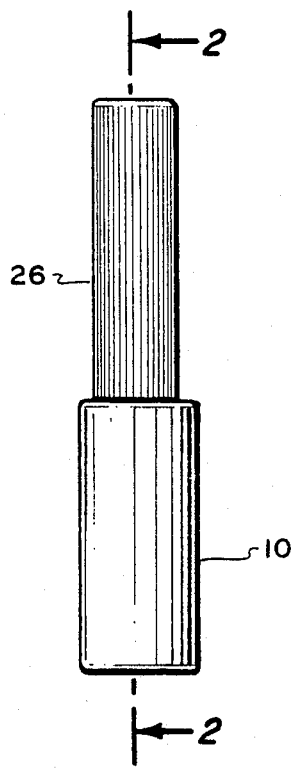
FIG. 1 is a longitudinal side elevational view of the container of the present invention.
Figure 2:
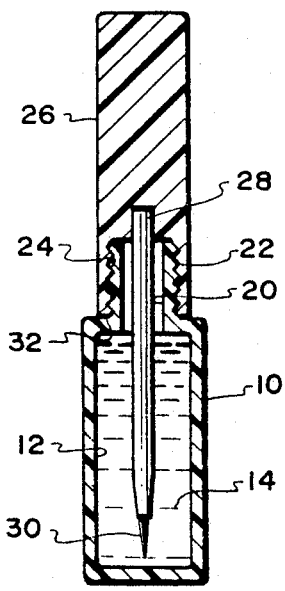
FIG. 2 is a cross-sectional view taken along line 2—2 of FIG. 1 which shows the cap being selectively mounted onto the container.
Figure 3:
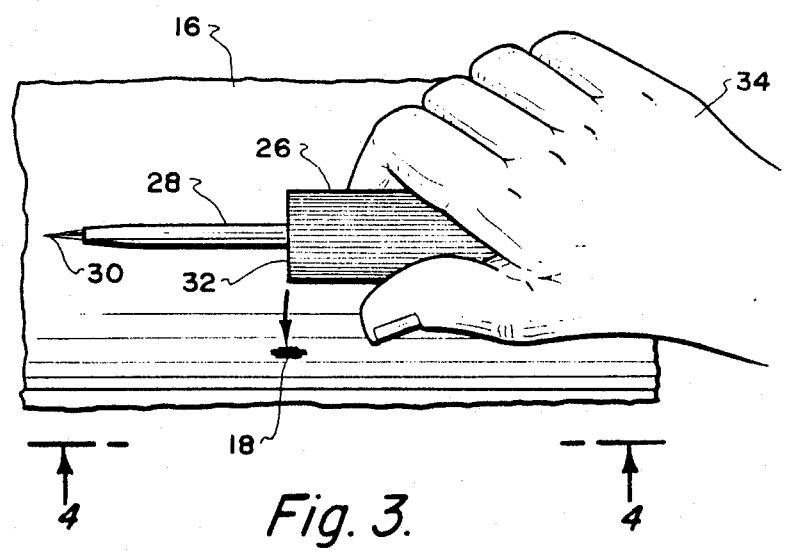
FIG. 3 is a top plan view of the cap portion of the container of FIG. 1 depicting the usage of such to select an injection site.
Figure 4:
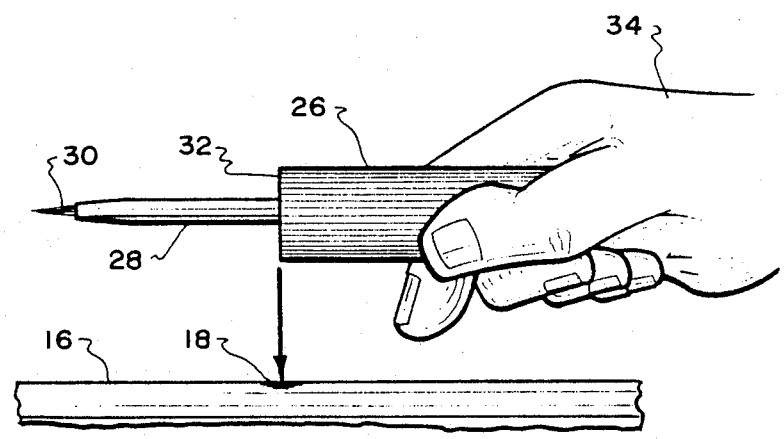
FIG. 4 is a side view taken along line 4—4 of FIG. 3.
Figure 5:
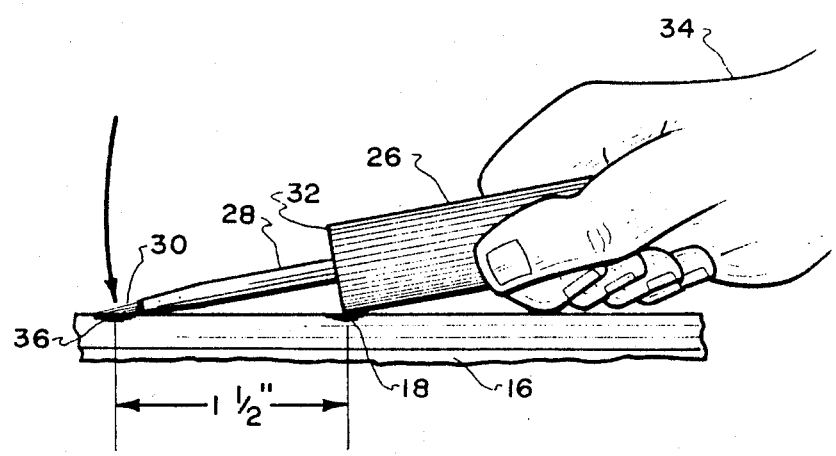
FIG. 5 is a view similar to FIG. 4 but showing the position of the cap in making of the mark that is required to denote the site of the next subsequent injection.

Referring particularly to the drawing, there is shown in FIG. 1 a container 10 of this invention which will normally be formed of a thin walled sheet material such as plastic. The container 10 includes an internal chamber 12 within which is located a quantity of an opaque liquid 14. The opaque liquid 14 is to be of a composition not readily dissolvable by water but will easily be dissolvable by an alcohol solvent. This non-dissolving of the liquid 14 by water will resist its removal by normal washing of the skin 16 of the human being. However, upon the application of alcohol, the opaque mark 18, as applied to the skin 16, is quickly and easily removed and the area is then sterilized which is a required initial procedure before injecting of the medicine through the skin 16.

The upper end of the container 10 includes an access opening 20. Surrounding the access opening 20 is an externally threaded collar 22. An internally threaded section 24 of a cap 26 is to threadingly engage with the threaded section of the collar 22. Fixedly mounted within the cap 26 is the inner end of a rod 28. The outer end of the rod 28 is connected to a pointed brush 30. The distance from the tip of the brush 30 to the forward edge 32 of the cap 26 is preselected to be of a particular distance. This desirable distance is one and one-half inches and is the minimum distance that is recommended between injection sites.

The user, shown by hand 34, is to remove cap 26 from the container 10. A small amount of the liquid 14 will remain on the brush 30. The user is to then place the forward edge 32 against the mark 18 which was previously applied to the skin 16 generally applied the day prior. The user then rocks the cap 26 until the brush 30 contacts the skin 16 thus forming another mark 36. The user then reconnects the cap 26 to the container 10. The user then removes the mark 18 with an alcohol solvent (not shown) and administers an injection through the use of a syringe (not shown) at exactly the point of the removed mark 18. It is to be known that the distance from the tip of the brush 30 to the forward edge 32 is slightly greater than one and one-half inches so the mark that is made by the brush 30 is one and one-half inches from the previous mark 18.

Various compositions of the liquid 14 can be utilized. In order for the marks 18 and 36 to resist removal by water, it is necessary that the liquid 14 penetrate the outer layer of the skin 16. The solvent used to remove the marks 18 and 36 must also penetrate the outer layer of the skin. The solvent alcohol, included in the composition, does penetrate the outer layer of the skin.

A preferable composition for the liquid 14 would be:

|  | by volume |
| --- | --- |
| Castor Oil | 20% |
| Kukui Oil | 17% |
| Stearic Acid | 10% |
| Triethanolamine | 1½% |
| Distilled Water | 45% |
| Cellulose Gum (Tragacanta) | 2% |
| Alcohol | 3% |
| Pigment for color (Black Iron Oxide) | 1½% |

The percent of the ingredients can vary, sixteen to twenty-two percent for the castor oil, fifteen to twenty percent for the kukui oil, five to ten percent for the stearic acid, and forty to sixty-five percent for the water.

The method of manufacture for this composition is as follows: The desired quantity of the castor oil, kukui oil and stearic acid are placed within a container, such as a water tub, and melted together at approximately 70° C. These three ingredients are evenly mixed together. The triethanolamine and water are heated to approximately 75° C. in a separate container and then mixed with the castor oil mixture. The cellulose gum, alcohol and pigment are mixed together in another separate container and then mixed with the water tube composition. With all ingredients now evenly mixed, the temperature is lowered to room temperature which causes this mixture to assume a thick creamy consistency.

What is claimed is:

1. The method of selecting a site for injection of medicine through the skin of a human being, said method comprising the steps of:

utilizing a container having a removable cap to which is attached a small brush extending a predetermined distance from said cap;

preloading said container with an opaque liquid which resists dissolving by water;

removing said cap and said brush from said container;

placing the edge of the cap nearest the brush against the skin at a selected location with the normal selected location being the site for the current injection;

rocking forward the brush until the brush contacts the skin leaving a small portion of the opaque liquid in the form of a small dot thereby to indicate to the human being the site for the subsequent injection;

removing the brush and the cap from the skin and replacing such on the container; and removing the opaque mark for the current injection by using an appropriate solvent and then administering the current injection.

* * * * *